(12) United States Patent
Ge et al.

(10) Patent No.: US 8,636,954 B2
(45) Date of Patent: Jan. 28, 2014

(54) CALIBRATION SLIDE FOR FLUORESCENCE DETECTION INSTRUMENTS AND PROCESS OF PREPARATION

(75) Inventors: Yu Ge, Beijing (CN); Wenjun Yang, Beijing (CN); Shuying Zhao, Beijing (CN); Lianghong Guo, Beijing (CN); Jing Cheng, Beijing (CN)

(73) Assignees: CapitalBio Corporation, Beijing (CN); Tsinghua University, Beijing (CN)

( * ) Notice: Subject to any disclaimer, the term of this patent is extended or adjusted under 35 U.S.C. 154(b) by 1413 days.

(21) Appl. No.: 11/660,469

(22) PCT Filed: Nov. 22, 2004

(86) PCT No.: PCT/CN2004/001328
§ 371 (c)(1),
(2), (4) Date: Dec. 28, 2007

(87) PCT Pub. No.: WO2006/007766
PCT Pub. Date: Jan. 26, 2006

(65) Prior Publication Data
US 2011/0318226 A1    Dec. 29, 2011

(30) Foreign Application Priority Data
Jul. 16, 2004    (CN) .......................... 2004 1 0069327

(51) Int. Cl.
*G01N 21/64*    (2006.01)
(52) U.S. Cl.
USPC ......... 422/82.08; 422/68.1; 436/81; 436/178; 436/807

(58) Field of Classification Search
USPC ................. 422/68.1, 82.08; 436/81, 178, 807
See application file for complete search history.

(56) References Cited

U.S. PATENT DOCUMENTS

| 4,777,133 A | 10/1988 | Picciolo et al. |
| 6,203,726 B1 | 3/2001 | Danielson et al. |

(Continued)

FOREIGN PATENT DOCUMENTS

| EP | 1 333 274 | 8/2003 |
| WO | WO-99/09415 | 2/1999 |
| WO | WO-00/69986 | 11/2000 |
| WO | WO-02/055997 | 7/2002 |
| WO | WO-02/077620 | 10/2002 |

OTHER PUBLICATIONS

Lu et al., "Synthesis and characterization of multi-functional nanoparticles possessing magnetic, up-conversion fluorescence and bio-affinity properties", J. Mater. Chem., 2004, 14, 1336-1341.*

(Continued)

*Primary Examiner* — Monique Cole
(74) *Attorney, Agent, or Firm* — Morrison & Foerster LLP

(57) ABSTRACT

The present invention relates to calibration slides for fluorescence detection instruments and processing method of making them. The aim of this invention is to disclose calibration slides with high photostability and long lifetime for fluorescence detection instruments. The calibration slides are fabricated by patterning calibration spot arrays of modified inorganic phosphors on the glass slide. The process for producing a calibration slide comprises the following procedure: 1) Dispersing the inorganic phosphors of rare-earth doped complex in water; 2) Patterning the array of the above suspension on the glass slide. The calibration slides in the present invention employ a very stable fluorescing material that is insensitive to photobleaching, has long lifetime and stability under mild storage condition. The calibration slides in the present invention can be used to calibrate and test for some fluorescence instruments, i.e. microarray scanner, fluorescent microscopy, fluorescence spectrometer, fluorescent multi-well-plate reader.

10 Claims, 3 Drawing Sheets

3 protection film
2 inorganic phosphors
1 glass substrate 2 inorganic phosphors
4 polymer film
1 glass substrate

(56) References Cited

U.S. PATENT DOCUMENTS

| | | |
|---|---|---|
| 6,402,986 B1 | 6/2002 | Jones et al. |
| 6,471,916 B1 | 10/2002 | Noblett |
| 6,472,671 B1 | 10/2002 | Montagu |
| 6,794,658 B2 * | 9/2004 | MacAulay et al. ......... 250/458.1 |
| 6,869,763 B1 * | 3/2005 | Tamura et al. ............... 435/6.11 |
| 2003/0015668 A1 | 1/2003 | Montagu |
| 2003/0049866 A1 | 3/2003 | Bushway et al. |
| 2003/0057379 A1 | 3/2003 | Montagu |
| 2003/0105195 A1 | 6/2003 | Holcomb et al. |

OTHER PUBLICATIONS

Schuetz et al., Electrostatically Assembled Fluorescent Thin Films of Rare-Earth Doped Lanthanum Phosphate Nanoparticles, Chem. Matter, 2002, 14, 4509-4516.*

Beverloo et al., "Inorganic Phosphors as New Luminescent Labels for Immunocytochemistry and Time-Resolved Microscopy", Cytometry 11:784-792 (1990).*

International Search Report for PCT/CN2004/001328, mailed on Jun. 9, 2005, 3 pages.

Database WPI Accession No. 2000-639266 (2000).

Liang et al., Journal of Alloys and Compounds (2004) 368(1-2):94-100.

Supplementary European Search Report for EP 04797359.9, mailed Dec. 15, 2009, 4 pages.

Communication pursuant to Article 94(3) EPC for EP 04797359.9, mailed Jan. 23, 2013.

Lu et al., "Synthesis and characterization of multi-functional nanoparticles possessing magnetic, up-conversion fluorescence and bio-affinity properties", J. Mater. Chem. (2004) 14:1336-1341.

* cited by examiner

Cy3 Channel  Cy5 Channel

Cy3 Channel  Cy5 Channel

CALIBRATION SLIDE FOR FLUORESCENCE DETECTION INSTRUMENTS AND PROCESS OF PREPARATION

CROSS-REFERENCE TO RELATED APPLICATIONS

This application is the national phase of PCT application PCT/CN2004/001328 having an international filing date of Nov. 22, 2004, which claims priority from China application number 200410069327.0 filed Jul. 16, 2004. The contents of these documents are incorporated herein by this reference in their entireties.

TECHNICAL FIELD

The present invention relates to calibration slides for fluorescence detection instruments and process of making them. More particularly, the present invention relates to rare-earth ion doped inorganic arrays for calibration of fluorescence microarray scanners and process of making them.

BACKGROUND ART

The arising of microarray technique since the end of last century has speeded the progress of Human Genome Project as well as many other research projects requiring high-through put analysis. Fluorescence microarray scanner has then become the most recently and successfully developed fluorescence detection instrument for the purpose of microarray chip analysis. But there appear two problems which affect its application in quantitative microarray analysis. For the individual scanners, the laser source inevitably fluctuates or even declines during operation and the confocal plane may also shift due to malfunctioned optical system, scanning accuracy also differs after long-term usage, which may cause error readings. For the instruments from different manufacturers, they differ in design and manufactory of light source, light path as well as the detection system, which results in incomparable readings. As all the other fluorescence detection instruments for quantitative analysis require routine calibration, fluorescence microarray scanner also needs to be calibrated to assure best performance. Thus, a calibration method for routine maintenance and data comparison between different instruments is inevitable. Fluorescence standard solutions have been used for calibration of fluorescence spectrometers and plate readers. However, they are not suitable for fluorescence microarray scanners which employ glass slide as detection targets. The object used as the calibration tool has to be easy to use, compatible to commonly used fluorescence channels in fluorescence microarray scanners, and most important, stable under long-term laser excitation.

At present, commonly used materials and means for calibration of fluorescence microarray scanners are as follows:

1. Organic fluorescent dyes as calibration material:

Gene Pharm Co. provides the Dilution Series Slide (DS3001) by directly printed Cy3, Cy5 dyes on the glass substrates to evaluate the stability of the laser scanner. The 20 serial dilutions cover several orders of concentration magnitude. Full Moon Biosystems produces similar calibration slide—FMB Microarray Scanner Calibration Slides. The slides are packaged in a vacuum-sealed bag and suggested to keep away from light at low temperature under dry condition.

Organic Fluorescence dyes possess poor photostability and will photo-bleach after exposure to light. The fluorescent intensity of the dyes (calibration dot) and thus shelf life of this kind of calibration slide are inevitable decreased after used in a relatively short time.

2. Organic Fluorescence Dyes Doped Polymers as Calibration Material:

Starna® fluorescence standards supplied by Optical Glass Limited are the reference materials to monitor fluorescence detection instrument performance and for standardization. Organic fluorescent dyes are dissolved in methylmethacrylate and the solution polymerized to produce a polymethylmethacrylate (PMMA) matrix, which provides a relatively stable environment for the enclosed organic fluorescent compounds. Polybead™ fluorescent polymer beads of Polysciences are used to calibrate the fluorescence spectrometer, flow pyrometer, plate reader etc. The organic fluorescent dyes are absorbed in the holes of polystyrene beads. Both the above two manufacturers don't mention calibration products for fluorescence microarray scanners. But in patent US2003/0105195, the inventor described the method of patterning the organic fluorescent dyes doped polymer matrix (PMMA, polyepoxide resin, polyamide) on the surface of a rigid slide to form a calibration slide for microarray scanners.

However, among these materials, the problem with photobleaching of fluorescent dyes still could not be resolved.

3. Broadband Fluorescence Emission Polymer as Calibration Material:

In the patents of US2003/0057379, US2003/0015668 and US6472671, a calibration tool for fluorescence microscopy is presented, which consists of a support of non-fluorescent quartz, a solid surface layer with a broadband fluorescence emitter, polyimide, and a thin opaque metal mask of non-fluorescent material. In a similar way, Clondiag Chip Technologies GmbH provides a novel array imaging standardization slide, which consists of an array of fluorescent spots with defined shape and intensity. In WO 02/077620, Clondiag patented manufacturing process guarantees stable fluorescence properties after ≧20 measurements. The fluorescent material is SU 8-10, a photo-sensitive broadband emitter polymer. Nevertheless, the polymer can also be photobleached under excitation, resulting in changes in the detected fluorescence intensity.

4. Organic Dye Doped Inorganic Solid Complex as Calibration Material:

US patent US2003/0015668 discloses a method to deposit an extremely thin layer of Cy3, Cy5 or other fluorescent dye doped glass by evaporation or sol-gel process on a non-fluorescent support and strengthened by baking at a relatively low temperature. But as the fluorescing material is again organic dye, simply encaged in inorganic matrix doesn't improve its photostability.

5. Inorganic Ion Doped Inorganic Solid Complex as Calibration Material:

Matech Co. provides fluorescent reference standards for 96 well plate readers. Each standard is made of a metal ion fluorophore doped in an inorganic glass host. The fluorescent ions used are $Ce^{3+}$, $U^{6+}$ and $Eu^{3+}$. Comparison photobleaching data between the rare-earth doped glass, rhodamine B and fluorescein in PMMA have been taken. During weeks of exposure to high intensity excitation light, both organic dyes show significant photobleaching, whereas the rare-earth doped glass shows little. However, the manufactory method restricts its application in calibration with fine structures for microarray scanners.

DISCLOSURE OF THE INVENTION

The aim of this invention is to disclose calibration slides with high photostability and long shelf life for fluorescence detection instruments and process of making them.

The present invention relates to calibration slides for calibration of fluorescence microarray scanners, which are fabricated by patterning calibration spot arrays of modified inorganic phosphors on the glass slide with the help of surfactants. The calibration slides in the present invention use rare-earth ions doped complex materials that is insensitive to photobleaching, possessing long lifetime and stability.

Preferably, the phosphor comprises a phosphor host and one or two other rare-earth ions with special luminescence properties. Any suitable phosphor host, e.g., yttrium, lanthanum or gadolinium, can be used in the present phosphor. Any suitable rare-earth ions, e.g., ytterbium, erbium, holmium, terbium or thulium, can be used in the present phosphor. In a specific embodiment, rare-earth ions doped phosphor has a formula of CaS:Eu, $NaYF_4$:Yb:M, $NaYF_4$:M, $NaYbF_4$:M and so on, where M=Tm, Er, Ho. The above complexes may be synthesized by precipitation or hydrothermal method and followed by annealed at high temperature.

The processing method of producing calibration slides may include more of the following:
1) Dispersing the rare-earth ions doped phosphor in water;
2) Patterning the array of the above suspension on the glass slide.

In one aspect, the inorganic phosphors are modified to improve their dispersing ability in water. Usually, inorganic materials could be coated with a transparent layer, e.g., a polystyrene layer, a $SiO_2$ layer. The transparent $SiO_2$ layer may be formed by hydrolysis of silane with the catalysis of acid or alkali. Any suitable silanization reagent can be used in the present processes, e.g., tetraethyl orthosilicate (TEOS), 3-aminopropyltriethoxysilane, 3-epoxypropyltriethoxysilane, 3-thiopropyltriethoxysilane. After the surface modification, inorganic phosphors show greatly enhanced hydrophilicity and dispersibility compared to uncoated materials.

In another aspect, surfactants or dispersants are employed to help the coated inorganic phosphors disperse evenly in aqueous suspensions. Preferably, surfactants may be polymeric dispersant. Any suitable one or mixture of the surfactants, e.g., Tween-20, Triton-100, sodium lauryl sulfate (SLS), polyethylene glycol (PEG) 2000, PEG 4000, PEG 6000, PEG 8000, PEG 10000, PEG 20000, polyvinyl alcohol (PVA), polyethylene imine (PEI), sodium polyacrylate (PAA) can be used in the suspension of the inorganic phosphors. The quantity of said surfactants may be 0.1%~10%, more preferably 0.1-5%.

In another aspect, any suitable spotting agent, e.g., dimethyl sulfoxide (DMSO) or glycerol is added in said suspension of inorganic phosphors. The calibration slide may be prepared by the following methods: calibration spot arrays of said inorganic phosphors are patterned on glass slide by microarray contact printer or by spin coating and screen printing techniques. The diameter of calibration spots is in the range of 100~500 μm, more preferably 120~300 μm.

The slides used in this invention with the dimension of 75.6 mm×25 mm×1 mm is a standard microscope glass slide, which may be unmodified or modified. Said glass slide is modified by chemical method, i.e. amino-modified slide, aldehyde-modified slide, epoxy-modified slide, thiol-modified slide or polymer film modified slide, i.e. PVA film, agarose film, or the mixing of PVA and agarose film.

A very thin layer can be deposited on the slide surface to protect the calibration spots of said inorganic phosphors. The embodiments of this aspect may be a transparent thin film of polydimethylsiloxane (PDMS) or PVA with low fluorescence background. The thickness of the film is less than 50 μm.

BRIEF DESCRIPTION OF THE DRAWINGS

FIG. 1A illustrates protecting polymer layer deposited on the calibration array on the glass slide. FIG. 1B illustrates the calibration array prepared on the glass slide modified with polymer film. Object 1 is a glass substrate slide; 2 is calibration array of inorganic phosphors; 3 is surface protecting layer; 4 is a polymer film.

EXAMPLES

Example 1

Preparation of Calibration Slides using Rare-Earth-$SiO_2$ Complex as Fluorescing Material 1. Preparation of Rare-Earth-$SiO_2$ Complex An aliquot of 2.2 ml of TEOS and 0.58 ml of anhydrous alcohol was mixed together and magnetically stirred in a 25 ml Erlenmeryer flask. Into the mixture, deionized water and 0.36 ml of 0.15 M hydrochloric acid aqueous solution was added dropwise to promote hydrolysis of TEOS. After reaction for 2 hours, a quantity of 10 ml of thulium chloride ($TmCl_3$) solution was added. The gel was aged for 12 hours at room temperature. Tm—$SiO_2$ complex was obtained after drying.

Four milligrams of the above said Tm—$SiO_2$ rare-earth inorganic complex were added to 100 μL of 4% PVA aqueous solution. The mixture was sonicated till the particles were well dispersed and used as printing sample. GeneMachine Contact Arrayer was used to print the printing sample onto the surface of a clean microscope slide to produce the calibration slides.

Figure 1:
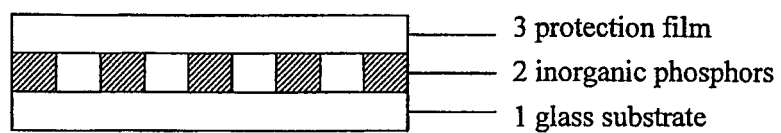
FIG. 1 depicts the construction structures of two calibration slides.
Figure 1:
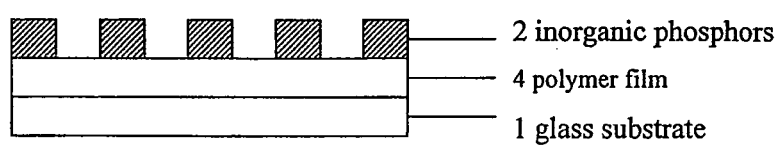
Figure 2:
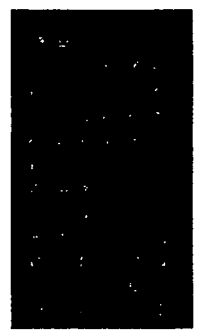
FIG. 2 illustrates the fluorescence scanning image of calibration slide fabricated by Tm doped $SiO_2$ complex.

The slide was scanned at Cy3 channel using a ScanArray 4000 biochip scanner. The fluorescence scanning image is shown in FIG. 2.

Example 2

Preparation of Calibration Slides using Rare-Earth Complex $NaYF_4$:Yb:Tm as Fluorescing Material 1. Preparation of $NaYF_4$:Yb:Tm Rare-Earth Complex A sodium fluoride (NaF) solution was prepared by dissolving 2.1 g of NaF in 80 ml of deionized water. Solutions of 20 ml of 0.2 M Yttrium chloride ($YCl_3$), 6 ml of 0.2 M ytterbium chloride ($YbCl_3$) and 3 ml of 0.2 M $TmCl_3$ were injected into the NaF solution. The mixture was stirred vigorously for 1 h at room temperature. The obtained precipitate was centrifuged at 4000 rpm, washed three times with deionized water, and dried at 60° C. The white powder of rare-earth complex was obtained after annealed at 400° C. for 5 h under nitrogen protection.

2. Preparation of Calibration Slide

The above said rare-earth complex was added to 10% Tween-20 aqueous solution. The calibration slides on clean glass slides were obtained following the same protocol as mentioned in Example 1.

Example 3

Preparation of Calibration Slides using Rare-Earth Complex $NaYF_4$:Tm as Fluorescing Material 1. Preparation of $NaYF_4$:Tm Rare-Earth Complex A NaF solution was prepared by dissolving 2.1 g of NaF in 80 ml of deionized water. Solutions of 20 ml of 0.2 M $YCl_3$ and 3 ml of 0.2 M $TmCl_3$ were injected into the NaF solution. The mixture was stirred vigorously for 1 h at room temperature. The obtained precipitate was centrifuged at 4000 rpm, washed three times with deionized water, and dried at 60° C. The white powder of rare-earth complex was obtained after annealed at 400° C. for 5 h under nitrogen protection.

2. Preparation of Aldehyde-Modified Slide

Five microscope slides were immersed in chromic acid solution (8 g $K_2Cr_2O_7$+5 ml $H_2O$+95 ml concentrated sulfuric acid) and cleaned thoroughly with Milli Q water. The slides were then immersed in 40 ml of 1% 3-aminopropyl triethoxysilane (APTES) ethanol solution for silanization. The reaction was continued for 1 h with rotation at 100 rpm to get amino-modified slides. The thus obtained amino-slides were then reacted with 8% glutaraldehyde aqueous solution for 1 h with rotation to get aldehyde-modified slides.

3. Preparation of Calibration Slides

The above said rare-earth rare-earth complex was added to 0.1% Triton-100 aqueous solution. The calibration slides on aldehyde-modified slides were obtained following the same protocol as specified in Example 1.

Example 4

Preparation of Calibration Slides using Rare-Earth Complex $NaYF_4$:Yb:Tm as Fluorescing Material 1. Preparation of $NaYF_4$:Yb:Tm Rare-Earth Complex Using Hydrothermal Method A NaF solution was prepared by dissolving 2.1 g of NaF in 80 ml of deionized water. Solutions of 20 ml of 0.2 M $YCl_3$, 6 ml of 0.2 M $YbCl_3$ and 3 ml of 0.2 M $TmCl_3$ were injected into the NaF solution. The mixture was stirred vigorously for 1 h at room temperature and then transferred to the hydrothermal reactor to continue to react for 2 h at 160° C. The obtained precipitate was centrifuged at 4000 rpm, washed three times with deionized water, and dried at 60° C. The white powder of rare-earth inorganic particles was obtained after annealed at 400° C. for 5 h under nitrogen protection.

2. Preparation of Thiol-Modified Slides

Five microscope slides were immersed in chromic acid solution and cleaned thoroughly with Milli Q water. The slides were then immersed in 40 ml of 1% 3-mercaptopropyl trimethoxysilane (MTPS) ethanol solution for silanization. The reaction was continued for 1 h with rotation at 100 rpm to get thiol-modified slides.

3. Preparation of Calibration Slide

The above said rare-earth complex was added to aqueous solution containing 5% PEG 2000 and 5% PEI. The calibration slides on thiol-modified slides were obtained following the same protocol as specified in Example 1.

Example 5

Preparation of Calibration Slides using Rare-Earth Complex $NaYF_4$:Yb:Tm as Fluorescing Material 1. Preparation of $NaYF_4$:Yb:Tm Rare-Earth Complex A NaF solution was prepared by dissolving 2.1 g of NaF in 80 ml of deionized water. Solutions of 20 ml of 0.2 M $YCl_3$, 6 ml of 0.2 M $YbCl_3$ and 3 ml of 0.2 M $TmCl_3$ were added into 20 ml of 0.2 M ethylenediamine tetraacetic acid sodium salt (EDTA-$Na_2$) aqueous solution and mixed thoroughly. The mixture was then quickly injected into the NaF solution and stirred vigorously for 1 h at room temperature. The obtained precipitate was centrifuged at 4000 rpm, washed three times with deionized water, and dried at 60° C. The white powder of rare-earth complex was obtained after annealed at 400° C. for 5 h under nitrogen protection.

2. $SiO_2$ Coating of the Rare-Earth Complex

An aliquot of 10 ml of isopropanol containing 40 mg of rare-earth complex was sonicated thoroughly, until a homogenous colloid-like suspension was obtained. Small amount of large-sized particles settled down at the bottom, and were discarded.

Approximately 40 ml of isopropanol was added to a 100 ml Erlenmeryer flask. It was magnetically stirred and annealed to 40° C. in an oil bath. The colloid-like homogenous rare-earth complex suspension was then added into the flask, with subsequent addition of 12 ml of deionized water and 20 ml of 25% ammonium hydroxide. The flask was then sealed. After the mixture was stirred for 10 min, 1 ml of TEOS was added into the flask and the reaction was kept on for 1 h. The mixture was transferred to centrifuge tubes and centrifuged at 4000 rpm. The supernatant was discarded and the pellet washed four times with deionized water. The resulting white powder was dried in oven at 60° C.

3. Preparation of Amine-Modified Slide.

Five microscope slides were immersed in chromic acid solution and cleaned thoroughly with Milli Q water. The slides were then immersed in 40 ml of 1% APTES ethanol solution for silanization. The reaction was continued for 1 h with rotation at 100 rpm to get amine-modified slides.

3. Preparation of Calibration Slide

Figure 3:
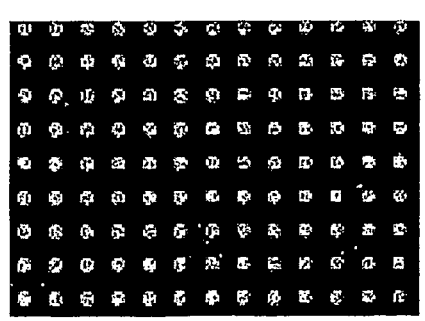
FIG. 3 illustrates the fluorescence scanning image of calibration slide prepared by the processing method described in Example 5.

The above said rare-earth complex was added to aqueous solution containing 4% PEG 2000 and 30% DMSO. The calibration slides on amine-modified slides were obtained using Cartesian Microarray Spotter. The slides were scanned at Cy3 channel using a ScanArray 4000 biochip scanner. The fluorescence scanning image is shown in FIG. 3.

Figure 4:
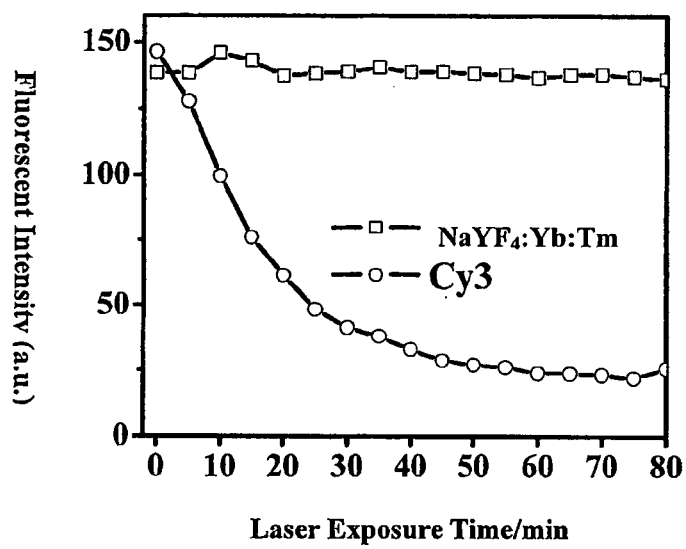
FIG. 4 shows the photostability comparison data between $NaYF_4$:Yb:Tm complex and Cy3 dye.

The photostability of the calibration spots made by the above rare-earth complex was compared with that of the fluorescent spots made by Cy3 dye purchased from Amersham Pharmacia. Both spots were exposed to 110 mW 532 nm laser. The fluorescent intensity of both spots was collected every five minutes. The result of the comparison is depicted in FIG. 4, which shows the rare-earth complex possesses superior photostability than Cy3 dye.

4. Preparation of PDMS Protection Film on Calibration Slide

Two components: Base and curing agent of Sylgard 184 provided by Dow Corning Co. Ltd were mixed at 10:1 (volume/volume) ratio and stirred thoroughly. The mixture was diluted by n-hexane. The protection film was prepared to fix the calibration spots on said slide surface by spin coating. The protection film was transparent, the thickness of which is about 40 μm.

Example 6

Preparation of Calibration Slides using Rare-Earth Complex $NaYF_4$:Tm as Fluorescing Material 1. Preparation of $NaYF_4$:Tm Complex Material Using Hydrothermal Method A NaF solution was prepared by dissolving 2.1 g of NaF in 80 ml of deionized water. Solutions of 20 ml of 0.2 M $YCl_3$ and 3 ml of 0.2 M $TmCl_3$ were injected into the NaF solution. The mixture was stirred vigorously for 30 min at room temperature. The suspension was transferred to the hydrothermal reactor and stained for 2 h at 160° C. The obtained precipitates were centrifuged at 4000 rpm, washed three times with deionized water, and dried at 60° C. The white powder of rare-earth fluorescent complexes was obtained after annealed at 400° C. for 5 h under nitrogen protection.

2. Surface Aminization of $NaYF_4$:Tm Complex

The above prepared $NaYF_4$:Tm complex was coated with $SiO_2$ following the same preparation method as shown in Example 5. Four hundred milligrams of the $SiO_2$ coated $NaYF_4$:Tm complex was added into the flask and sonicated for 1 h. A quantity of 0.07 mmol (1.2 ml) of APTES was then added into the reaction system and the suspension was stirred for an additional 3 h. The mixture was transferred to centrifuge tubes and centrifuged at 12,000 rpm. The supernatant was discarded and pellet washed twice with deionized water. The resulting white powder was dried in oven at 60° C.

3. Preparation of Epoxy-Modified Slide

Five microscope slides were immersed in chromic acid solution and cleaned thoroughly with Milli Q water. The slides were then immersed in 40 ml of 1% 3-glycidoxypropyl trimethoxysilane (GPTS) ethanol solution for silanization. The reaction was continued for 1 h with rotation at 100 rpm to get epoxy-modified slides.

4. Preparation of Calibration Slides

The above said rare-earth fluorescent complex was added to aqueous solution containing 2% SLS and 3% PAA. The calibration slides on epoxy-modified slides were obtained following the same protocol as specified in Example 1.

Example 7

Preparation of Calibration Slides for Marking of Scanning Area

Figure 5:
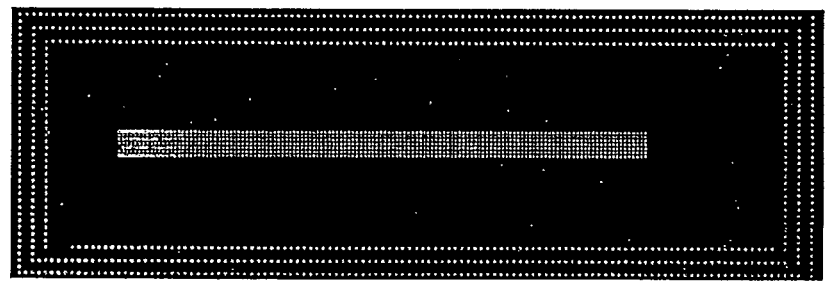
FIG. 5 illustrates the fluorescence scanning image of calibration slide for geometric marking prepared by the processing method described in Example 7.

The rare-earth complex prepared in Example 5 was dispersed with sonication in aqueous solution containing 4% PEG 8000 and 30% DMSO and used as printing sample to print on amine-modified glass slides using GeneMachine Arrayer. The fluorescence scanning image was obtained using a ScanArray 4000 biochip scanner at Cy3 channel and is shown in FIG. 5. This slide can be used for marking scanning area of microarray chips.

Example 8

Preparation of Calibration Slides with Different Fluorescence Intensity Levels

Figure 6:
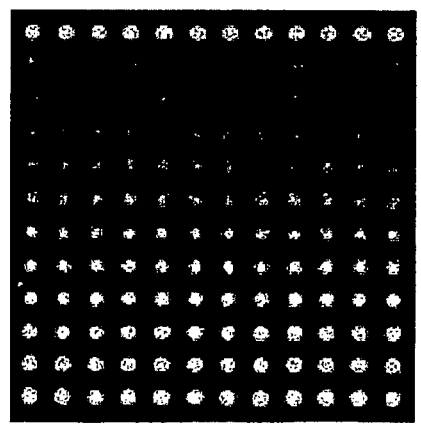
FIG. 6 illustrates the fluorescence scanning image of calibration slide with spots of different intensity levels prepared by the processing method described in Example 8.

The rare-earth complex prepared in Example 5 was dispersed with sonication in aqueous solution containing 30% DMSO and 5% glycerol to get a stock suspension. The final solid content of the suspension was kept at 12%. The stock suspension was then diluted stepwise to suspensions with solid contents of 9%, 6.75%, 5.06%, 3.8%, 2.85%, 2.14%, 1.6%, 1.2%, 0.9% and 0.68%, respectively. All suspensions were sonicated and then used as printing samples. Three identical arrays were printed using Catesian Microarray Spotter with a ϕ110 μm steel pin on an aldehyde-modified slide. The fluorescence scanning image at Cy3 channel is shown in FIG. 6. The first row are printed spots with solid content of 12%, and the second till twelfth row correspond to printed spots with solid content of 0.68%, 0.9%, 1.2%, 1.6%, 2.14%, 2.85%, 3.8%, 5.06% 6.75%, 9%, 12%, respectively.

Example 9

Preparation of Calibration Slides with Polyvinylalcohol Protection Layer

Figure 7:
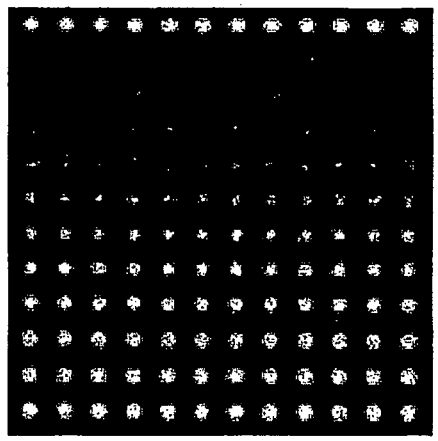
FIG. 7 illustrates the fluorescence scanning image of calibration slide with PVA protection film on the surface prepared by the processing method described in Example 9.

In order to prevent calibration spots from dropping off the glass slide surface, PVA protection layer was constructed. The calibration slide was dipped into 0.2% PVA aqueous solution for several seconds, taken out, and let dry. The fluorescence scanning image at Cy3 channel was obtained using a ScanArray 4000 biochip scanner and was shown in FIG. 6. The PVA protection layer guarantees the intact of the calibration spots during everyday usage and doesn't change their fluorescence emission intensity, nor the homogeneity, as shown by the comparison of scanning images in FIG. 6 and FIG. 7.

Example 10

Preparation of Calibration Slides using CaS:Eu as Fluorescing Material

1. Synthesis of CaS:Eu Complex $Eu_2O_3$ was dissolved in concentrated nitric acid with magnetic stirring and heating. Excess nitric acid was evaporated. The obtained $Eu(NO_3)_3$ solution was diluted with ethanol and mixed with $CaCl_2$ ethanol solution before use.

Two hundred milliliters of $Na_2S$ ethanol solution was added into a three-neck flask and vigorously stirred under nitrogen protection. Fifty milliliters of $Eu(NO_3)_3/CaCl_2$ mixture solution was quickly injected into the $Na_2S$ solution. The mixture was stirred vigorously for 1 h at room temperature. The obtained precipitate was centrifuged at 4000 rpm, washed five times with deionized water, and dried at 60° C. overnight. The pink powder of rare-earth inorganic particles was obtained after annealed at 700° C. for 3 h under nitrogen protection.

2. Preparation of CaS:Eu Calibration Slide

Figure 8:
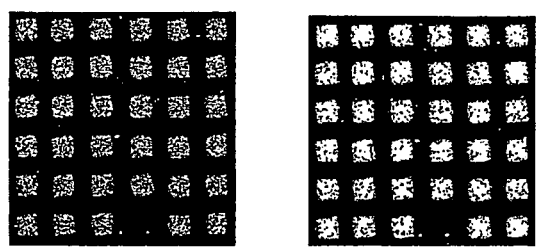
FIG. 8 illustrates the fluorescence scanning image of calibration slide in Cy3 and Cy5 channels prepared by the processing method described in Example 10.
Figure 9:
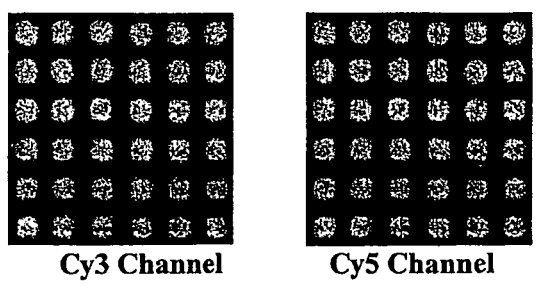
FIG. 9 illustrates the fluorescence scanning image of calibration slide prepared by the processing method described in Example 11.

CaS:Eu sample was suspended in 1% PEG 8000 aqueous solution, and printed onto a clean microscope slide using GeneMachine Arrayer. The fluorescence scanning images taken at both Cy3 and Cy5 channels were obtained using a ScanArray 4000 biochip scanner and are shown in FIG. 8.

Example 11

Preparation of Calibration Slides using PVA Film Modified Slides as Substrates

1. Preparation of a PVA Film Modified Slide

A spin coater was used to spin 2% PVA ($M_w$~80,000) aqueous solution onto a clean glass slide surface. The slide was air dried at room temperature.

2. Preparation of the Calibration Slide

SiO$_2$ coated rare-earth complex obtained in Example 5 was suspended in aqueous solution containing 10% glycerol and 1% PEG 8000. Calibration slide was obtained following method shown in Example 7 on a PVA film modified slide. The fluorescence scanning image at Cy3 channel is shown in FIG. 11.

Example 12

Preparation of Calibration Slides using Agarose Film Modified Slides as Substrates 1. Preparation of an Agarose Film Modified Slide A spin coater was use to spin 1% agarose aqueous solution onto a clean glass slide surface. The slide was air dried at room temperature.

2. Preparation of a Calibration Slide

SiO$_2$ coated rare-earth particles obtained in Example 5 were suspended in aqueous solution containing 10% glycerol and 1% PEG 20000. Calibration slide was obtained following method shown in Example 7 on an agarose film modified slide.

Example 13

Preparation of Calibration Slides using PVA-Agarose Complex Film Modified Slides as Substrates 1. Preparation of a PVA-Agarose Complex Film Modified Slide A spin coater was used to spin aqueous solution containing 2% PVA and 1% agarose onto a clean glass slide surface. The slide was air dried at room temperature.

2. Surface Coating of Rare-Earth Complex with Polystyrene

One hundred milligram of inorganic rare earth complex obtained in Example 6 was added into three-neck flask containing 20 ml of toluene, followed by addition of 0.1 g of SDS and sonicated for 0.5 h. Fifty milligram of benzoyl peroxide, 0.5 ml of styrene and 0.3 ml of divinylbenzene were then added. The reaction system was pulsed with nitrogen, mixed with a steel stirrer for 15 minutes and annealed with an oil bath. The mixture was kept at 80° C. and stirred slowly overnight. The three-neck flask was first cooled down to room temperature and supernatant discarded. The precipitate was collected in a centrifuge tube and centrifuged at 1000 rpm, washed with ethanol, then deionized water, and dried at 60° C.

3. Preparation of the Calibration Slide

Polystyrene coated rare-earth complex was suspended in aqueous solution containing 10% glycerol and 1% PEG 6000, and printed on the surface of a PVA-agarose complex film modified slide, following the method specified in Example 7. The slide was annealed at 50° C. for 7 days and the calibration slide was obtained.

Example 14

Preparation of Calibration Slide using Rare-Earth Complex NaYbF$_4$:Tm as Fluorescing Material 1. Preparation of NaYbF$_4$:Tm Rare-Earth Complex A NaF solution was prepared by dissolving 2.1 g of NaF in 80 ml of deionized water. Solutions of 6 ml of 0.2 M YbCl$_3$ and 3 ml of 0.2 M TmCl$_3$ were injected into the NaF solution. The mixture was stirred vigorously for 1 h at room temperature. The obtained precipitate was centrifuged at 4000 rpm, washed three times with deionized water, and dried at 60° C. The white powder of NaYbF$_4$:Tm complex was obtained after annealed at 400° C. for 5 h under nitrogen protection.

2. Preparation of a Calibration Slide

The above said rare-earth complex was coated with SiO$_2$ following the method specified in Example 5 and was suspended in aqueous solution containing 1% PVA and 4% PEG 2000. A spin coater was used to spin the suspension on a clean glass slide surface. The slide was air-dried with a thickness of surface coating of about 20 μm. Screen printable polymeric composition (e.g. Dupont 5036 paste) was used to screen print the spin-coated surface. After polymerization at 80° C. for 20 minutes, calibration arrays with identical ϕ500 μm spots were obtained.

Example 15

Preparation of Calibration Slide using Rare-Earth Complex NaYF$_4$:Yb:Er as Fluorescing Material 1. Preparation of NaYF$_4$:Yb:Er Rare-Earth Complex A NaF solution was prepared by dissolving 2.1 g of NaF in 80 ml of deionized water. Solutions of 20 ml of 0.2 M YCl$_3$, 6 ml of 0.2 M YbCl$_3$ and 3 ml of 0.2 M ErCl$_3$ were injected into the NaF solution. The mixture was stirred vigorously for 1 h at room temperature. The obtained precipitate was centrifuged, washed three times with deionized water, and dried at 60° C. The white powder of NaYF$_4$:Yb:Er complex was obtained after annealed at 400° C. for 5 h under nitrogen protection.

2. Preparation of a Calibration Slide

The above complex material was coated with SiO$_2$ following the method specified in Example 5. The coated sample was suspended in aqueous solution containing 4% PEG 2000 and 30% DMSO and printed on amine-modified surface using a Cartesian Microarray Spotter to get the calibration slide.

Example 16

Preparation of Calibration Slide using NaYF$_4$:Yb:Ho Rare-Earth Complex as Fluorescing Material 1. Preparation of NaYF$_4$:Yb:Ho Rare-Earth Complex A NaF solution was prepared by dissolving 2.1 g of NaF in 80 ml of deionized water. Solutions of 20 ml of 0.2 M YCl$_3$, 6 ml of 0.2 M YbCl$_3$ and 3 ml of 0.2 M HoCl$_3$ were injected into the NaF solution. The mixture was stirred vigorously for 1 h at room temperature. The obtained precipitate was centrifuged, washed three times with deionized water, and dried at 60° C. The white powder of NaYF$_4$:Yb:Ho complex was obtained after annealed at 400° C. for 5 h under nitrogen protection.

2. Preparation of Calibration Slide

The above said rare-earth complex material was coated by SiO$_2$ and suspended in aqueous solution containing 4% PEG 2000 and 30% DMSO. The calibration slide was obtained by printing the suspended sample on amino-modified slide using a Cartesian Microarray Spotter.

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

The invention claimed is:

1. A calibration slide for a fluorescent instrument comprising a microarray of an inorganic phosphor regularly arranged with stepwise fluorescent intensity levels on a glass slide; said inorganic phosphor comprises rare-earth metal multiplex materials, wherein said rare-earth metal multiplex materials comprise a rare-earth ion doped phosphor having the formula of CaS:Eu, $NaYF_4$:Yb:M, $NaYF_4$:M, $NaYbF_4$:M, said M is Tm, Er or Ho.

2. The calibration slide of claim 1, wherein said rare-earth ion doped phosphor is coated with a polymer or an inorganic layer, wherein said polymer layer includes polystyrene and said inorganic layer comprises $SiO_2$.

3. The calibration slide of claim 1, wherein said slide is an unmodified glass slide or a modified glass slide by chemical method or by polymer film modification.

4. The calibration slide of claim 3, wherein said slide modified by chemical method is selected from the group consisting of a amine-modified slide, an aldehyde-modified slide, an epoxy-modified slide, and a thiol-modified slide; wherein said polymer film is selected from the group consisting of a PVA film, an agarose film and a PVA-agarose complex film.

5. The calibration slide of claim 1, wherein said calibration slide comprises a protecting layer deposited on the surface, wherein said protecting surface layer comprises PDMS and PVA.

6. A calibration slide for a fluorescent instrument comprising a microarray of an inorganic phosphor on a glass slide; said inorganic phosphor comprises rare-earth metal multiplex materials, wherein said rare-earth metal multiplex materials comprise a rare-earth ion doped phosphor having the formula of CaS:Eu, $NaYF_4$:Yb:M, $NaYF_4$:M, $NaYbF_4$:M, said M is Tm, Er or Ho.

7. A calibration slide for a fluorescent instrument comprising a microarray of an inorganic phosphor on a glass slide; said inorganic phosphor comprises rare-earth metal multiplex materials, wherein said rare-earth ion doped phosphor is coated with a polymer or an inorganic layer, wherein said polymer layer includes polystyrene and said inorganic layer comprises $SiO_2$.

8. The calibration slide of claim 6, wherein said slide is an unmodified glass slide or a modified glass slide by chemical method or by polymer film modification.

9. A calibration slide for a fluorescent instrument comprising a microarray of an inorganic phosphor on a glass slide; said inorganic phosphor comprises rare-earth metal multiplex materials, wherein said calibration slide comprises a protecting layer deposited on the surface, wherein said protecting surface layer comprises PDMS and PVA.

10. The calibration slide of claim 8, wherein said slide modified by chemical method is selected from the group consisting of a amine-modified slide, an aldehyde-modified slide, an epoxy-modified slide, and a thiol-modified slide; wherein said polymer film is selected from the group consisting of a PVA film, an agarose film and a PVA-agarose complex film.

* * * * *